United States Patent
Sefton

(10) Patent No.: US 9,206,451 B2
(45) Date of Patent: Dec. 8, 2015

(54) CHEMOAUTOTROPHIC CONVERSION OF CARBON OXIDES IN INDUSTRIAL WASTE TO BIOMASS AND CHEMICAL PRODUCTS

(75) Inventor: Brian Sefton, Cupertino, CA (US)

(73) Assignee: Oakbio, Inc., Sunnyvale, CA (US)

( * ) Notice: Subject to any disclaimer, the term of this patent is extended or adjusted under 35 U.S.C. 154(b) by 0 days.

(21) Appl. No.: 13/610,844

(22) Filed: Sep. 11, 2012

(65) Prior Publication Data
US 2013/0065285 A1 Mar. 14, 2013

Related U.S. Application Data

(60) Provisional application No. 61/533,672, filed on Sep. 12, 2011, provisional application No. 61/640,459, filed on Apr. 30, 2012.

(51) Int. Cl.
C12M 1/36 (2006.01)
C12P 7/62 (2006.01)
C12M 1/00 (2006.01)
(Continued)

(52) U.S. Cl.
CPC . *C12P 7/62* (2013.01); *B01D 53/62* (2013.01); *B01D 53/85* (2013.01); *C12M 29/06* (2013.01); *C12M 43/04* (2013.01); *C12P 7/18* (2013.01); *C12P 7/625* (2013.01); *C12P 7/64* (2013.01); *C12P 23/00* (2013.01); *B01D 2251/102* (2013.01); *B01D 2251/202* (2013.01);
(Continued)

(58) Field of Classification Search
CPC ......... C12P 7/62; C12M 43/04; C12M 29/06; C12M 41/34; C12M 41/40; C12M 23/24; C12M 41/14; C12M 27/02; C12M 35/04; C12M 1/04; C12M 23/14; C12M 29/10; Y02E 50/13

USPC ............................. 435/135, 266, 286.6, 289.1
See application file for complete search history.

(56) References Cited

U.S. PATENT DOCUMENTS 3,402,225 A * 9/1968 Cameron ..................... 106/754
5,230,803 A 7/1993 Thuer et al.
(Continued)

FOREIGN PATENT DOCUMENTS

| CA | 2280086 A1 | 8/1998 |
| CN | 101525551 A | 9/2009 |

(Continued)

OTHER PUBLICATIONS

PCT/US10/27850 International Search Report and Written Opinion, mailed Jul. 28, 2010.
(Continued)

*Primary Examiner* — Michael Hobbs
(74) *Attorney, Agent, or Firm* — Peters Verny, LLP

(57) ABSTRACT

Systems and methods for employing chemoautotrophic micro-organisms to capture carbon from industrial waste are provided. An exemplary system comprises an industrial source, such as a cement plant, and a bioreactor including the micro-organisms. The bioreactor is fed the waste stream from the source, which provides carbon to the micro-organisms, and is also fed hydrogen, from which the micro-organisms derive their energy. Additional or alternative carbon can be provided from a gasifier fed an organic feedstock. The carbon provided to the micro-organisms is converted into chemical products which can be recovered from the bioreactor. Hydrogen can be produced by electrolysis using electricity generated by a renewable energy source.

24 Claims, 8 Drawing Sheets

(51) Int. Cl.
*C12P 23/00* (2006.01)
*C12P 7/18* (2006.01)
*C12P 7/64* (2006.01)
*B01D 53/62* (2006.01)
*B01D 53/85* (2006.01)

(52) U.S. Cl.
CPC ... *B01D2257/504* (2013.01); *B01D 2258/0233* (2013.01); *Y02E 50/13* (2013.01)

(56) References Cited

U.S. PATENT DOCUMENTS

| | | | |
|---|---|---|---|
| 5,686,276 | A | 11/1997 | Laffend et al. |
| 7,250,288 | B2 | 7/2007 | Zeikus et al. |
| 8,349,587 | B2 | 1/2013 | Fischer et al. |
| 8,518,566 | B2 | 8/2013 | Sefton |
| 2005/0247553 | A1* | 11/2005 | Ichikawa et al. ............. 202/96 |
| 2006/0051848 | A1 | 3/2006 | Nishio et al. |
| 2007/0099062 | A1 | 5/2007 | Leonida |
| 2007/0259216 | A1 | 11/2007 | Logan |
| 2007/0259217 | A1 | 11/2007 | Logan |
| 2008/0277273 | A1 | 11/2008 | Logan |
| 2008/0292912 | A1 | 11/2008 | Logan et al. |
| 2009/0317882 | A1 | 12/2009 | Cheng et al. |
| 2010/0018214 | A1* | 1/2010 | Halachmi Katchanov ..... 60/772 |
| 2010/0120104 | A1* | 5/2010 | Reed ............................ 435/140 |
| 2010/0200495 | A1 | 8/2010 | Borole et al. |
| 2010/0227203 | A1 | 9/2010 | Ter Heijne et al. |
| 2010/0229725 | A1* | 9/2010 | Farsad et al. ..................... 96/74 |
| 2010/0298450 | A1 | 11/2010 | Datta et al. |
| 2012/0288898 | A1 | 11/2012 | Lovley et al. |
| 2013/0078690 | A1 | 3/2013 | Reed |
| 2013/0089899 | A1 | 4/2013 | Kurek |

FOREIGN PATENT DOCUMENTS

| | | |
|---|---|---|
| WO | 2007073598 A1 | 7/2007 |
| WO | 2009111513 A1 | 9/2009 |
| WO | 2011088425 A2 | 7/2011 |
| WO | 2012116338 A1 | 8/2012 |

OTHER PUBLICATIONS

EP 12 831 884.7 Amendment in Response to Rules 161(2) and 162 EPC Communication, submitted Jun. 5, 2014.
U.S. Appl. No. 13/204,649 Applicant's Amendment C, submitted May 20, 2014.
U.S. Appl. No. 13/204,649 Advisory Action, mailed Jun. 4, 2014.
U.S. Appl. No. 13/204,649 Applicant's Amendment D, submitted Jun. 26, 2014.
U.S. Appl. No. 13/034,596 Applicant's Amendment C, submitted Jun. 17, 2014.
Pulse and Alternating Currents http://www.ee.sc.edu/personal/faculty/simin/ELCT102/15%20Pulse%20 &%20AC%20Circuits,%20Capacitors.pdf downloaded online Apr. 3, 2014.
Watkinson et al., Metallurgical Transactions B 13B: 369-378 (1982).
U.S. Appl. No. 12/726,980 non-final Office action, mailed Jan. 16, 2013.
U.S. Appl. No. 12/726,980 Applicant's Amendment B, submitted Apr. 16, 2013.
U.S. Appl. No. 12/875,708 non-final Office action, mailed Dec. 4, 2012.
U.S. Appl. No. 13/034,596 non-final Office action, mailed Apr. 9, 2014.
U.S. Appl. No. 13/204,649 non-final Office action, mailed Aug. 27, 2013.
U.S. Appl. No. 13/204,649 Applicant's Amendment B, submitted Dec. 18, 2013.
U.S. Appl. No. 13/204,649 final Office action, mailed Mar. 26, 2014.
Goh, Ee-Been, et al., "Engineering of Bacterial Methyl Ketone Synthesis for Biofuels," Appl. Environ. Microbiol. 2012, 78(1)70, Oct. 28, 2011.
PCT/US12/54822 International Search Report and Written Opinion, mailed Jan. 16, 2013.
EP 12831884.7 Extended European Search Report, mailed Jun. 5, 2015.
Jiun-Yee Chee et al., "Bacterially Produced Polyhydroxyalkanoate (PHA): Converting Renewable Resources into Bioplastics," Current Research, Technology and Education Topics in Applied Microbiology and Microbial Biotechnology A., Mendez-Vilas (Ed.), pp. 1395-1404, Jan. 1, 2010.
EPO First Examination Report, Application No. 12 749 555.4, Dated Jul. 23, 2015.
Greene, et al., "Artificially evolved *Synechococcus* PCC6301 Rubisco variants exhibit improvements in folding and catalytic efficiency", Biochemical Journal, 2007, vol. 404, pp. 517-524.
Office Action, CN Application No. 2012800547760, Dated Aug. 12, 2015.

\* cited by examiner

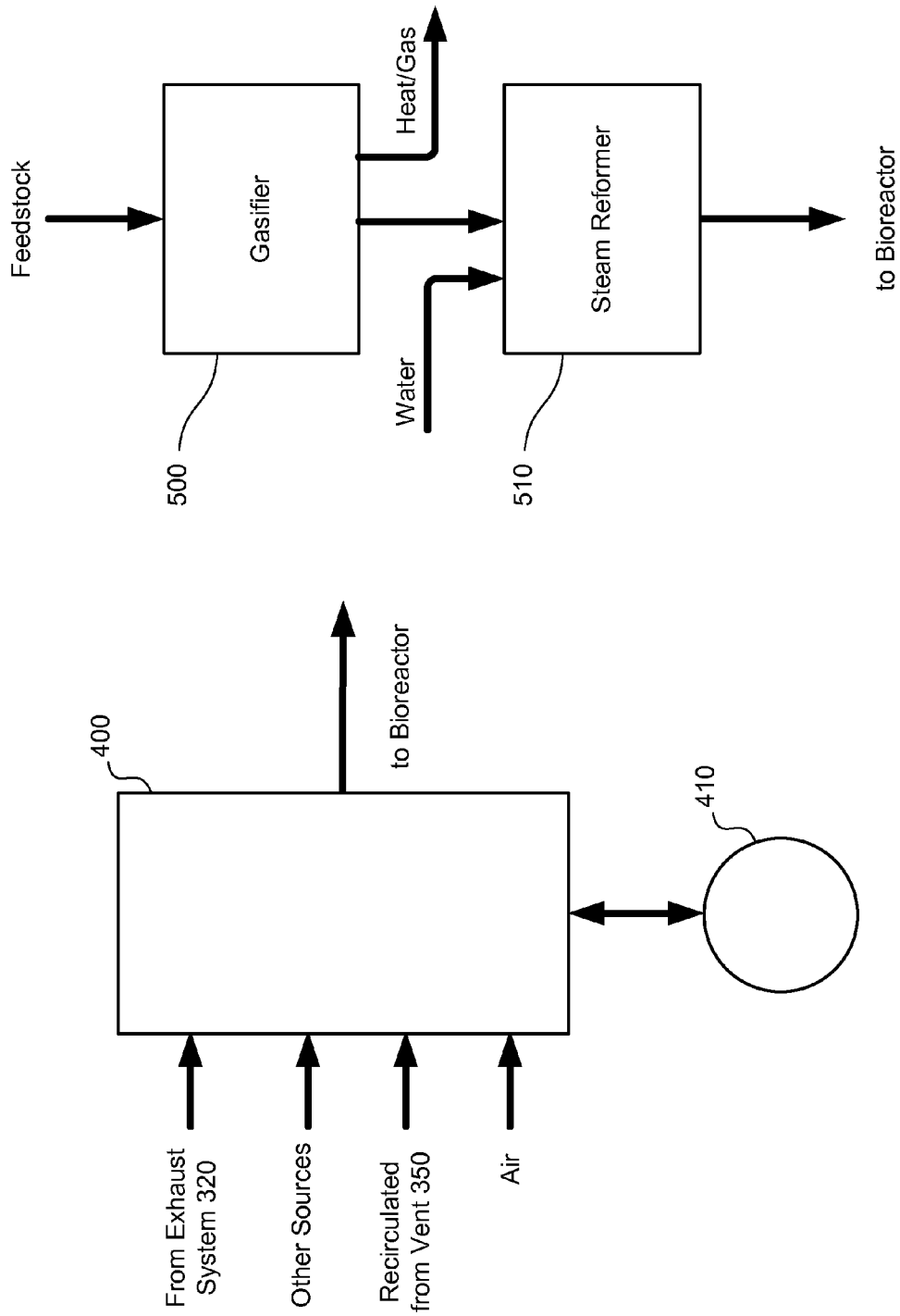

CHEMOAUTOTROPHIC CONVERSION OF CARBON OXIDES IN INDUSTRIAL WASTE TO BIOMASS AND CHEMICAL PRODUCTS

CROSS-REFERENCE TO RELATED APPLICATIONS

This application claims the benefit of U.S. Provisional Patent Application Ser. No. 61/533,672 filed on Sep. 12, 2011 and entitled "Methods and Microbes for Industrial Greenhouse Gas Capture and Production of Chemicals and Biomass by Chemoautotrophic Microbes" and U.S. Provisional Patent Application Ser. No. 61/640,459 filed on Apr. 30, 2012 and entitled "Chemoautotrophic Methods and Microbes for Carotenoid Synthesis," both of which are incorporated herein by reference.

BACKGROUND OF THE INVENTION

1. Field of the Invention

The present invention relates generally to bioreactor systems and more particularly to methods for their use in the chemoautotrophic synthesis of chemical products from carbon captured from industrial waste streams.

2. Description of the Prior Art

The reliance on petrochemicals as a primary feedstock for the creation of products such as plastics, cosmetics, lubricants, adhesives, paints, transportation fuels and many other commodity, specialty, and fine chemicals is increasingly under scrutiny due both to the resultant production of greenhouse gases, and the high and variable cost of the petroleum feedstock. Renewable chemicals derived from microbial sources offer environmentally sustainable alternatives to those derived from fossil resources.

Microbes require a source of carbon in order to live, grow and produce chemical products. Many industrial sources produce large amounts of carbon, primarily in waste gases as one or both of the carbon oxides, carbon dioxide ($CO_2$) and carbon monoxide (CO). Carbon oxides from industrial sources are primarily produced by the combustion of fossil fuels and/or chemicals and are classified as greenhouse gases due to their contribution to deleterious environmental conditions. Thus, capturing carbon oxides from industrial gas effluent is both a potentially cheap and scalable way to obtain carbon for biologically mediated chemical production, and a way to reduce the amount of carbon dioxide released into the atmosphere.

Cement manufacture is a major source of atmospheric carbon dioxide, as well as other greenhouse gases. In cement production, a mineral feedstock is progressively heated to increasingly higher temperatures, causing a succession of chemical reactions to take place. One of these reactions is calcination, also referred to as calcining, in which the carbonate-bearing minerals within the feedstock decompose, releasing carbon dioxide. The decomposition of calcium carbonate, for example, is represented as follows:

$$CaCO_3 \rightarrow CaO + CO_2.$$

Further reactions at even higher temperatures yields a "clinker" which is a sintered mass that is then ground to an appropriate fineness for cement.

In addition to the carbon dioxide generated by the carbonate mineral decomposition in calcination process, above, cement production also generates carbon dioxide in further ways. For instance, mechanical processing such as crushing and grinding and the high temperatures used to produce the final clinker, all tend to be achieved by the combustion of fossil fuels.

Accordingly, cement manufacturing produces at least two carbon waste streams. The first stream principally comprises the carbon dioxide from carbonate decomposition. Water vapor (steam) is a major impurity in this first stream as water in the raw mineral feedstock is also driven off. Other impurity gases vary with the particular composition, purity and contaminants in the raw mineral feedstock.

The second carbon waste stream comprises carbon dioxide, carbon monoxide, and other gases produced by the combustion of feedstock fuels for heating and running motors for conveyors and grinders, for example. These fuels are often fossil fuels, but can also be fuels derived from the combustion or gasification of biomass, waste materials, or other fuel sources. The exact composition of this gas in the second stream is dependent upon the composition of the fuel feedstock in use.

The compositions of both the first and second gas streams are also affected by the uses of air and sometimes the use of other gases. For example, both streams tend to include nitrogen and oxygen from the atmosphere since calcining is typically performed in air and air typically provides the oxygen for combustion. Cement plant flue gas often also contains oxides of sulfur and nitrogen, referred to generally as $SO_x$ and $NO_x$, as well as hydrogen sulfide and other greenhouse gases.

The production of renewable chemicals involves the capture of carbon oxides and their incorporation into chemical products. Microbial systems offer environmentally sustainable, greenhouse-gas-sparing, and highly energy, water, and carbon-efficient, chemical manufacturing processes for the capture of carbon oxides. Microbial chemical production can be local in most areas, and can be co-located with carbon releasing industries such as cement manufacturing. By using carbon captured from the waste streams of industry (whether gas, liquid or solid waste), it is possible to produce truly carbon neutral, renewable, replacements for petroleum products. This also reduces dependence on imported fossil energy resources.

Fermentation is a well-known process wherein chemical compounds such as sugars are provided as feedstock. In fermentation, sugars are broken down to produce commercially useful, but lower energy, products like ethanol. Such chemical feedstock provides the source of carbon, essential for building up new compounds and allowing microbial metabolism and growth (anabolism), and the chemical bond energy that is used to drive the process energetically. This type of metabolism is called heterotrophic and has historically dominated the use of diverse bacteria and fungi to make chemicals useful to society.

Another type of microbial metabolism, called autotrophic, refers to the use of inorganic carbon sources, primarily captured carbon dioxide, as the primary source of carbon. These inorganic carbon sources provide the essential carbon source but embody significantly less chemical energy than sugars used in heterotrophic growth. Photoautotrophic organisms, including the green plants and algae, use light energy to drive the capture of carbon dioxide. The term "chemoautotrophic" pertains to organisms that derive both their energy and their carbon from inorganic chemical sources.

Chemoautotrophic metabolism describes a metabolic mode in which the organism uptakes inorganic carbon, such as by capturing carbon dioxide, as a primary carbon source, and obtains energy from a chemical source, such as by oxidizing hydrogen. Chemoautotrophic metabolism is primarily found in a number of bacteria, including, but not limited to purple non-sulfur (PNS) bacteria such as *Rhodobacter capsulatus, Rhodobacter sphaeroides, Rhodpsuedamonas palustris*, the betaproteobacteria, such as *Ralstonia metallidurans (Ralstonia eutropha.)*, the pseudomonas, such as *Pseudomonas carboxydovorans*, the methanogenous bacteria, such as *Methanobacterium thermoautotrophicum*, the betaproteobacteria, such as *Ralstonia metallidurans, Ralstonia eutropha*, the acetogenous bacteria, such as *Acetobacterium woodii*, or other microbes which express both an uptake hydrogenase and a carbon dioxide fixation metabolism, whether endogenous or introduced through genetic manipulation, mutation, selection or directed evolution, such as *Escherichia coli, Anabaena, Bacillus subtilus*, etc. In many cases these microbes are capable of heterotrophic as well as phototrophic metabolism, or mixed metabolism using both sources of energy and carbon. In some cases molecular hydrogen ($H_2$) is used as the energy source, and carbon dioxide is used as the carbon source. Carbon monoxide can also act as a possible energy source and as a possible carbon source, but carbon monoxide generally works best in a mix with hydrogen and/or carbon dioxide and/or oxygen, due to its toxicity.

Gasification is a process where biomass, fossil fuels, or other carbon containing materials are subjected to high temperature and a restricted supply of air or oxygen in a controlled reactor called a gasifier. This process, referred to as pyrolysis when oxygen is not provided, produces a number of gasses, principally including carbon monoxide and hydrogen but may also produce one or more of carbon dioxide, water vapor, methane, ethylene, and ethane. Pyrolysis at lower temperatures is known as torrefaction. Gas streams produced by gasification have large amounts of carbon monoxide and can be further processed to convert the carbon monoxide and water into carbon dioxide and hydrogen via several processes referred to as reforming processes, notably steam reforming. Reforming techniques include, but are not limited to, steam reforming, catalytic reforming, and biologically mediated reforming such as biocatalysed electrolysis or fermentative hydrogen production. Furthermore, molecular hydrogen and carbon monoxide are major components of syngas, where varying amounts of carbon monoxide and molecular hydrogen are generated by gasification of a carbon-containing fuel. For example, syngas may be produced by cracking the organic biomass of municipal waste, waste water solids, waste woods, timber, plastics, and non-biodegradable carbon containing materials, to generate precursors for the production of fuels and more complex chemicals.

SUMMARY

According to the present invention, chemoautotrophic micro-organisms in an aqueous medium in a bioreactor, which contains no significant alternative sources of energy, derive both their primary energy and carbon from molecular hydrogen and a carbon oxide added to the bioreactor. The carbon oxide can be produced as a waste product of an industrial process, such as cement manufacturing. The carbon oxide can additionally, or alternatively, be provided from the gasification of an organic feedstock, which may then be reformed. The carbon provided to the micro-organisms is converted by the micro-organisms into useful chemical products which per unit weight contain more energy, and are more valuable than the gaseous inputs. Methods of the present invention also produce 'green' cement; cement which is either carbon neutral or at least produced with a process where less greenhouse gases are released into the atmosphere during manufacture. Furthermore, methods of the present invention allow the use of alternate fuel sources in cement manufacture, and providing for the capture and utilization of effluent gases, which would not normally be practical from a regulatory and/or cost basis. Alternative sources of energy include gasified coal, biomass or waste materials, and fuel oils as well as directly combusted materials of many types. Furthermore methods of the present invention provide for the improvement of the process by methods for blending gases. These methods for blending gases are of particular utility when used with the effluent gas produced by cement manufacture.

An exemplary system of the present invention comprises a bioreactor and an industrial source producing a waste stream including a carbon oxide such as cement manufacturing, power generation, and so forth. The bioreactor comprises a first substrate comprising the waste stream, a second substrate comprising molecular hydrogen, and a liquid medium including a culture of a micro-organism capable of chemoautotrophically capturing at least some of the carbon oxide in the first substrate, such as *Rhodobactor capsulatus* and/or *Ralstoni eutropha*. Some embodiments of the system include a source of the second substrate, such as a storage tank or an electrolysis system. The electrolysis system can be disposed within the bioreactor, in some instances. Some embodiments that include an electrolysis system also include a renewable electricity source in electrical communication with the electrolysis system. Various embodiments further comprise a separation system configured to receive the liquid medium from the bioreactor and to separate biomass and/or a chemical product from the received liquid medium.

Some embodiments of the present invention further comprise a gas mixing unit in fluid communication between the industrial source and the bioreactor. In these embodiments, the gas mixing unit is configured to mix the waste stream from the industrial source with another gas stream, such as from a gasifier, to produce the first substrate for the bioreactor. Some embodiments that comprise the gas mixing unit also comprise a storage system in fluid communication with the gas mixing unit. Since the carbon in the first substrate is the source of carbon for the micro-organism culture, the storage system can provide the first substrate in instances where the industrial source is not producing.

Various embodiments also comprise a gasifier and a reformer where the reformer is configured to receive the gaseous output from the gasifier and wherein the bioreactor is configured to receive the gaseous output of the reformer. Heat and/or some of the gaseous output from the gasifier can also be diverted to other uses. In some of these embodiments the reformer is further configured to receive a second gas stream in addition to the gaseous output from the gasifier, for example, steam from process cooling. In embodiments where the reformer receives steam, the reformed can be a steam reformer. In various embodiments the reformer can also be a catalytic reformer.

Another exemplary system of the present invention comprises a cement manufacturing facility and a bioreactor system. The cement manufacturing facility includes a cement kiln and an exhaust gas system configured to capture the exhaust gas from the cement kiln, while the bioreactor system includes a bioreactor in fluid communication with the exhaust gas system and configured to produce a chemical product from a carbon oxide in a first gaseous stream from the exhaust gas system, the first gaseous stream including the exhaust gas from the cement kiln. The bioreactor system can also include a separation system configured to receive a liquid medium from the bioreactor and to separate the chemical product from the received liquid medium. The exemplary system optionally also comprises a gasifier configured to generate a second gaseous stream, and a reformer configured to receive the second gaseous stream and to produce a third gaseous stream, wherein the bioreactor is in fluid communication with the reformer to receive the third gaseous stream. In some of these embodiments, the reformer is further configured to receive at least some of the first gaseous stream from the cement manufacturing facility such that a fluid communication path between the bioreactor and the exhaust gas system includes the reformer.

In various embodiments, the system also comprises a gas mixing unit in fluid communication between the bioreactor and the exhaust gas system. Some of these systems further comprise an electrolysis system configured to produce a molecular hydrogen stream, and wherein the gas mixing unit is configured to receive the molecular hydrogen stream. In some of these later embodiments the electrolysis system is further configured to produce a molecular oxygen stream, and the gas mixing unit is configured to receive the molecular oxygen stream independent from the molecular hydrogen stream. Some embodiments that include the gas mixing unit further comprise a controller configured to monitor a condition in the bioreactor, such as pH, temperature, gas composition, and so forth, and further configured to regulate the flow of gases into the gas mixing unit responsive to the condition.

An exemplary method of the invention comprises providing a carbon oxide to a bioreactor, providing molecular hydrogen to the bioreactor, and optionally providing molecular oxygen to the bioreactor, and maintaining a culture of a chemoautotrophic micro-organism in a growth medium in the bioreactor, the micro-organism being capable of chemoautotrophically capturing at least part of the carbon oxide to produce a chemical product. In some embodiments, providing the carbon oxide to the bioreactor includes communicating a waste stream from an industrial process to the bioreactor. Likewise, in some embodiments providing the carbon oxide to the bioreactor includes gasifying an organic feedstock to produce a gasified output, subjecting the gasified output to reforming to produce a reformed output, and communicating the reformed output to the bioreactor.

In various embodiments the step of providing molecular hydrogen includes generating the molecular hydrogen. In some of these embodiments generating the molecular hydrogen includes employing reforming, such as steam reforming or catalytic reforming. Likewise, in some embodiments generating the molecular hydrogen includes employing electrolysis of water. In some of these later embodiments, generating the molecular hydrogen further comprises generating electricity for the electrolysis of the water, and in some of these embodiments the electrolysis is performed within the bioreactor.

Optionally, the exemplary method also comprises growing the chemoautotrophic micro-organism culture before maintaining the culture in the bioreactor. The exemplary method also can comprise separating a chemical product from the growth medium, and in some of these embodiments the chemical product comprises a hydroxyalkanoate or a polyhydroxyalkanoate, for example. In various embodiments the exemplary method also comprises separating a biomass from the growth medium; in these embodiments gasifying the organic feedstock includes gasifying the biomass. In various embodiments the molecular hydrogen is provided in a range of about 60% to about 80% by volume, the carbon oxide is provided in a range of about 5% to about 20% by volume, and the molecular oxygen is provided in a range up to about 30% by volume.

BRIEF DESCRIPTION OF DRAWINGS

FIG. 4 is a schematic representation of an exemplary mixer and storage system usable in conjunction with systems of the present invention.

FIG. 5 is a schematic representation of an exemplary gasifier and steam reformer usable in conjunction with systems of the present invention.

DETAILED DESCRIPTION OF THE INVENTION

The present invention is directed to the chemoautotrophic conversion of waste carbon into useful products such as biomass and/or chemicals in order to provide economically viable, environmentally attractive, and sustainable processes for capturing greenhouse gases and to produce therefrom chemical products and/or biomass at scale. More specifically, carbon monoxide and/or carbon dioxide in industrial waste can be fed, together with molecular hydrogen, to chemoautotrophic micro-organisms in a bioreactor; the micro-organisms employ the hydrogen as their source of energy. The micro-organisms use the energy to capture carbon and to grow, reproduce, and generate by-products, their own waste stream. Both the biomass and these by-products, typically organic compounds, can be harvested.

Deposit of Biological Material

The following microbes have been deposited with the American Type Culture Collection, 10801 University Boulevard, Manassas Va. 20110-2209, USA (ATCC):

TABLE 1

| Microbe Designation | ATCC No. | Deposit Date |
| --- | --- | --- |
| *Rhodobacter capsulatus* OB-213 | PTA-12049 | Aug. 25, 2011 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Oakbio, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

Figure 1:
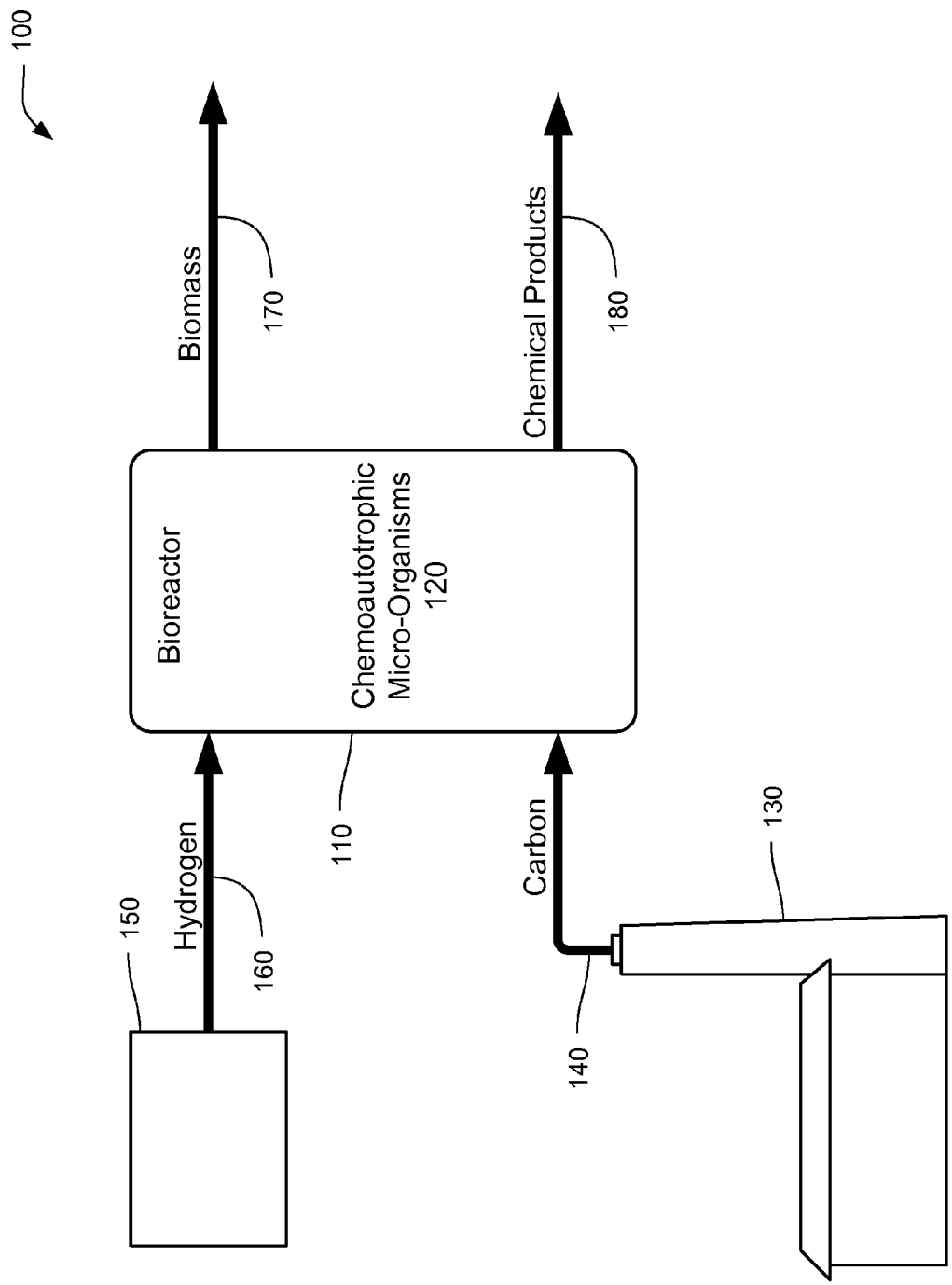
FIG. 1 is a schematic representation of a system according to an exemplary embodiment of the present invention.

FIG. 1 shows a schematic representation of an exemplary system 100 of the invention. The system 100 comprises a bioreactor 110 including a chemoautotrophic micro-organism culture 120. The system 100 also comprises a source of carbon 130, such as an industrial source that produces a waste stream 140 including one or more of the carbon oxides, carbon monoxide and carbon dioxide. Examples of sources of carbon 130 include cement manufacturing facilities, power plants that burn fossil fuels, ferrous metal products manufacturing (e.g., casting and forging), non-ferrous products manufacturing, foodstuffs manufacturing, gasification of biomass, gasification of coal, and chemical manufacturing such as petroleum refining, carbon black production, ammonia production, methanol production and coke manufacturing. The waste stream 140 contributes to a first substrate fed into the bioreactor 110. The first substrate can simply be the waste stream 140 itself, or can comprise the waste stream 140 in combination with other components, such as mixed with air.

Figure 7:
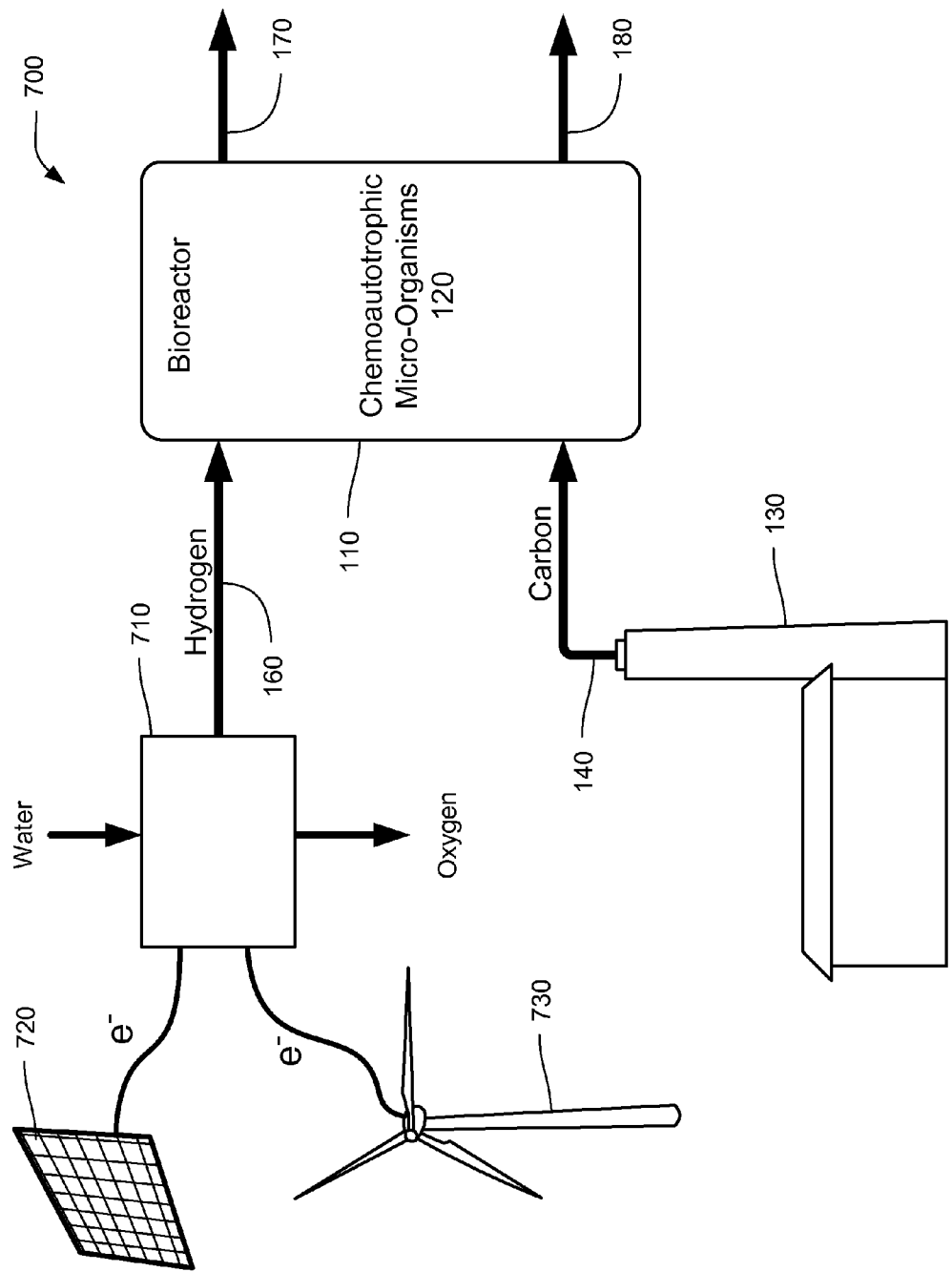
FIG. 7 is a schematic representation of a system according to another exemplary embodiment of the present invention.

The system 100 further comprises a source of molecular hydrogen 150, such as a hydrogen storage tank or an electrolysis system (see FIG. 7). The hydrogen source 150 produces a hydrogen stream 160 including molecular hydrogen. The hydrogen stream 160 contributes a second substrate to the bioreactor 110. The second substrate can likewise simply be the hydrogen stream 160 itself, or can comprise the hydrogen stream 160 in combination with other components. The system 100 can further comprise one or more additional sources 150 of molecular hydrogen contributing to the second substrate.

While FIG. 1 shows the two substrates fed into the bioreactor 110 separately, the substrates may be combined prior to introduction into the bioreactor 110. As used herein, the term "substrate" is used consistent with the commonly understood meaning in biochemistry, namely, "the material which a micro-organism ingests to grow." The ratio of the rates at which the substrates are provided to the bioreactor 110 are controlled, in some embodiments, to optimize the overall composition fed to the culture 120 and/or to achieve a desired overall effluent gas composition.

Substrates can be gaseous, liquid, or solid. A liquid substrate can be saturated with a carbon oxide containing gas, or saturated with molecular hydrogen, or both. This may be achieved using standard methodologies, such as, for example, a micro-bubble dispersion generator (see Hensirisak et. al., "Scale-up of Microbubble Dispersion Generator for Aerobic Fermentation," *Applied Biochemistry and Biotechnology* Volume 101, Number 3/October, 2002, incorporated herein by reference).

The chemoautotrophic micro-organism culture 120 is capable, under proper conditions within the bioreactor 110, of capturing at least some, and in some instances most or all, of the carbon oxides in the first substrate to create a biomass 170 and/or chemical products 180. In some embodiments, such proper conditions do not require light and therefore in some embodiments the bioreactor 110 does not include a source of artificial lighting. Natural lighting may be used as an additional energy source, or excluded. In other embodiments, natural or artificial light can be used selectively to stimulate or influence a metabolic pathway. Two characteristics of microbe candidates for application in this process are the expression of uptake hydrogenases, such as the Nickel-Iron (NiFe), Hydrogenases, often written as '[NiFe]Hydrogenases; in their outer membrane, and the expression of a carbon oxide capture system, such as provided by Rubisco, in their outer cell membrane, in carboxysomes or microcompartments, which are able to receive energy from the hydrogenases or carbon monoxide capture. Suitable micro-organisms for the culture 120 include bacteria such as purple non-sulfur (PNS) bacteria like *Rhodobacter capsulatus, Rhodobacter sphaeroides, Rhodpsuedamonas palustris*; the betaproteobacteria, such as *Ralstonia metallidurans (Ralstonia eutropha.)*; the pseudomonas, such as *Pseudomonas carboxydovorans*; the methanogenous bacteria, such as *Methanobacterium thermoautotrophicum*; the betaproteobacteria, such as *Ralstonia metallidurans* and *Ralstonia eutropha*; the acetogenous bacteria, such as *Acetobacterium woodii*; and any other microbe which expresses both an uptake hydrogenase and a carbon dioxide fixation metabolism, whether endogenous or introduced through genetic manipulation, mutation, selection or directed evolution, such as *Escherichia coli, Anabaena, Bacillus subtilus*, etc.

Examples of the chemical products 180 that can be produced by the chemoautotrophic conversion include organic compounds such as hydroxyalkanoates and polyhydroxyalkanoates like hydroxybutyric acid and polyhydroxybutyric acid as well as heteropolymers which contain various mixes of hydroxybutyrate and hydroxyvalerate, the alkanoate diols, propanediol, octadecane 1,12 diol, and carotenoids, fatty acids, fats, oils, and alkanes. Some exemplary polyhydroxyalkanoates comprise 3-hydroxybutyrate monomers or hydroxybutyrate and hydroxyvalerate monomers. Polyhydroxyalkanoates can be transformed by a variety of methods, including depolymerization, into other substances such as monomers, fatty acid methylesters, and other polymers.

Some chemical products 180 can be further transformed into other substances such as biofuels like butanol, ketones, methylesters, alkanes, biodiesel, fatty acids and polytrimethylene like polytrimethylene terephthalate and various biofuels. Chemical products 180 comprise, in some embodiments, polyhdroxyalkanoates, carotenoids, lipopolysaccharides, a mixed alcohol stream containing one or more alkanoate diols and one or more other alcohols, or a variety of other chemicals, and can be recovered from the chemoautotrophic synthesis broth by methods known in the art. By-products such as acids including acetate and butyrate may also be recovered from the culture broth using methods known in the art. Biomass 170 harvested from the bioreactor 110 can also be a useful commodity as it can be converted to biofuel, used as animal feed, as a colorant, as an additive for products for use with humans and/or animals for cosmetic or nutritional purposes, turned to compost, gasified, and so forth.

A bioreactor 110 for chemoautotrophic synthesis can comprise one or more vessels and/or towers or piping arrangements, and can comprise, for example, a Continuous Stirred Tank Reactor (CSTR), an Immobilized Cell Reactor (ICR), a Trickle Bed Reactor (TBR), a Bubble Column, a Gas Lift Fermenter, a Static Mixer, a Fluidized Bed, an Up-flow or Down-flow, a continuous, batch or loop reactor, or any other vessel or device suitable for maintaining suitable gas-liquid contact. In some embodiments, the bioreactor 110 may comprise a first growth vessel and a second chemoautotrophic synthesis vessel, while in other embodiments a single vessel is used throughout both of the growth and synthesis stages.

Additional bioreactor designs that can be used in conjunction with the present invention can be found in U.S. patent application Ser. No. 13/204,649 filed on Aug. 6, 2011 and entitled "Chemoautotrophic Bioreactor Systems and Methods of Use" which is incorporated herein by reference.

In the growth stage, a small quantity of the chemoautotrophic micro-organism culture 120 is grown into a suitable concentration for the subsequent synthesis stage in which the chemoautotrophic micro-organism culture 120 is used to produce the biomass 170 and/or one or more chemical products 180. The conditions in the bioreactor 110 in the two stages are generally different and the culture 120 can receive different substrates. In those embodiments in which the bioreactor 110 comprises growth and synthesis vessels, a broth from the growth vessel is fed into the synthesis vessel in which the chemoautotrophic synthesis product (biomass 170 and/or chemical products 180) is produced.

Figure 2:
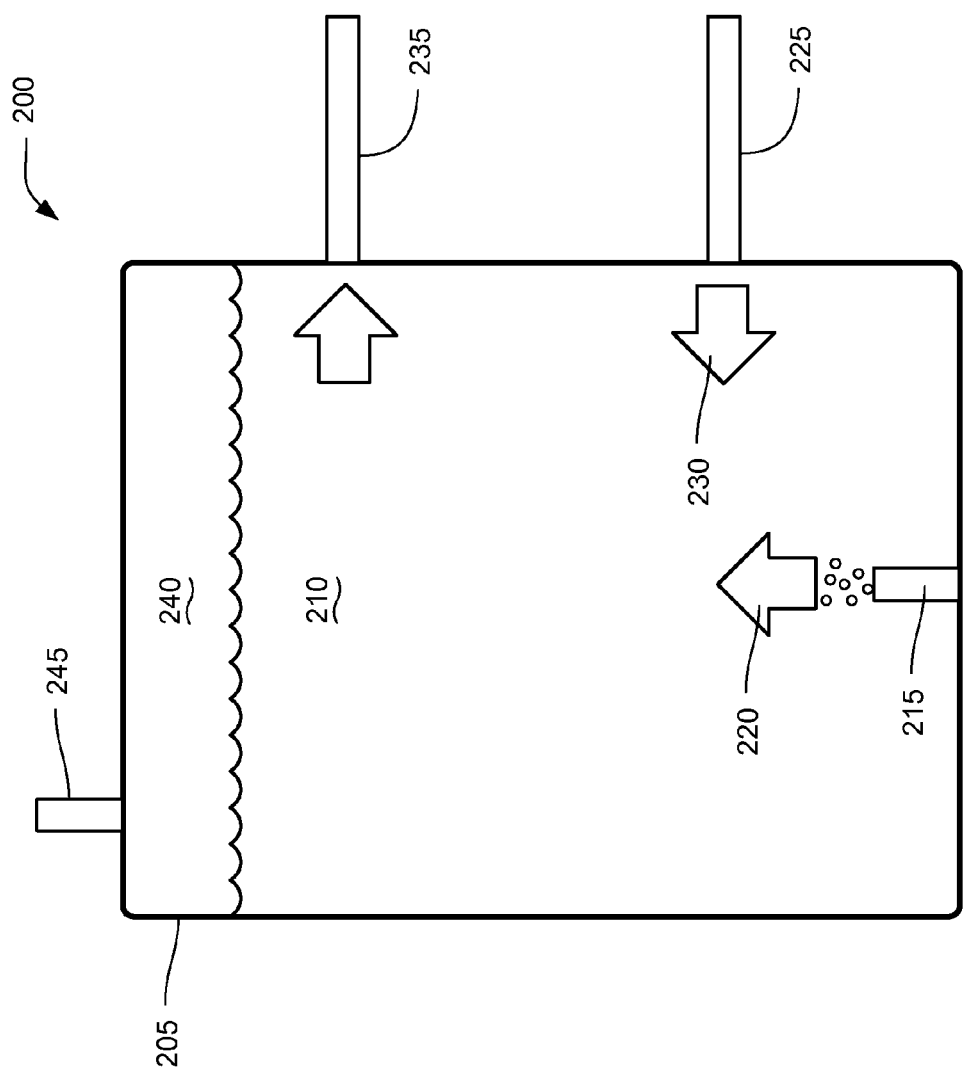
FIG. 2 is a schematic representation of a bioreactor according to an exemplary embodiment of the present invention.

FIG. 2 shows a schematic representation of a bioreactor 200 as one example of a bioreactor 110 that is suitable for continuous culture. Bioreactor 200 can comprise either a synthesis vessel for use in conjunction with a separate growth vessel, or can comprise a vessel suitable for both of the growth and synthesis stages. In FIG. 2, bioreactor 200 includes a vessel 205 that in operation holds a quantity of a liquid medium 210 containing the chemoautotrophic micro-organism culture 120. The bioreactor 200 also includes a substrate port 215 through which a gaseous substrate 220 can be introduced into the vessel 205 for introduction into the liquid medium 210, a media inlet port 225 through which fresh media 230 can be introduced into the vessel 205 for introduction into the liquid medium 210, and a media outlet port 235 through which the medium 210 can be removed, for example, to harvest biomass 170 and/or chemical products 180. The bioreactor 200 can also comprise a headspace 240 and a gas release valve 245 to vent gases from the headspace 240. In some embodiments the media outlet port 235 and the media inlet port 225 are connected via a system which harvests biomass 170 and/or chemical products 180 and reconditions the medium 210 for recirculation (see FIG. 3). In some embodiments the gas release valve 245 is attached to a system which re-circulates the gaseous substrate back to the substrate port 215, and may make additions or subtractions to optimize the gas composition.

Returning to FIG. 1, it will be appreciated that the culture 120 requires a suitable medium (i.e., medium 210) in addition to the two substrates. A suitable medium 210 contains components, such as vitamins, minerals, and micronutrients necessary and sufficient to sustain the culture 120. Some of these components may be optimized for increasing product yield. Chemoautotrophic media suitable for the growth of *Rhodobacter capsulatus* are known in the art, as described for example by Madigan and Gest, "Growth of the Photosynthetic Bacteria *Rhodopsuedomonas capsulata* chemoautotrophically in the Dark with $H_2$ as the Sole Energy Source," J. of Bacteriology, 524-530 January 1979, incorporated herein by reference.

Figure 3:
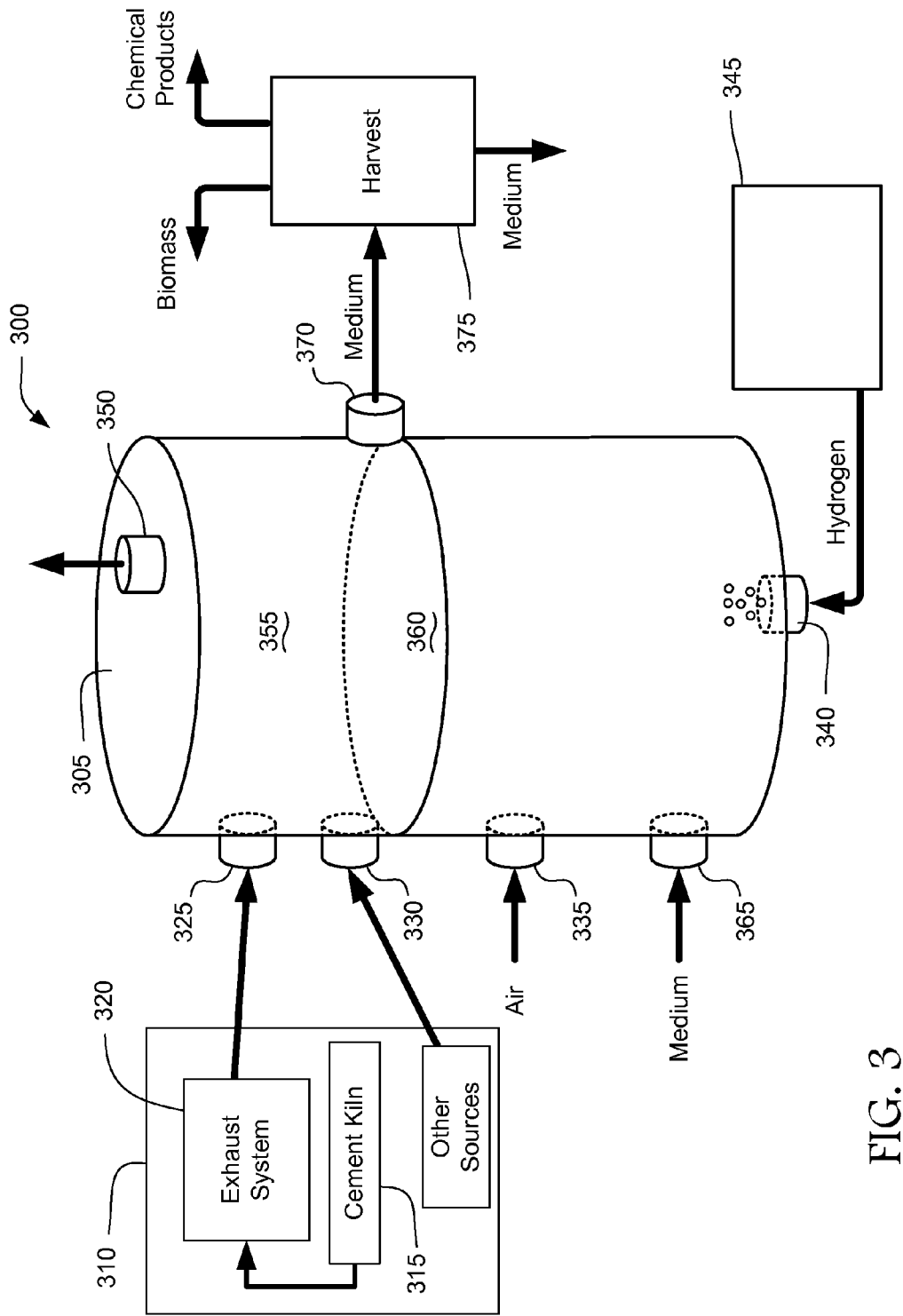
FIG. 3 is a schematic representation of a system according to another exemplary embodiment of the present invention.

FIG. 3 shows a schematic representation of another exemplary system 300. The system 300 comprises a bioreactor 305 as another example of a bioreactor 110. The system 300 also comprises a cement manufacturing facility 310, and the bioreactor 305 is located proximate to, and is in fluid communication with the cement manufacturing facility 310 to receive waste carbon therefrom. The cement manufacturing facility 310 includes a cement kiln 315 within which a mineral feedstock is progressively heated to yield a clinker, and an exhaust gas system 320 configured to capture the exhaust gas of the cement kiln 315. Heating can be achieved, for example, through the combustion, gasification, or pyrolysis of fossil fuels such as petroleum coke.

Although not shown in FIG. 3, it will be understood that the facility 310 includes other components such as pre-heaters, motor-driven equipment to convey materials and drive grinders, and so forth. The exhaust gas produced by the cement kiln 315 includes the carbon dioxide released within the cement kiln 315 from carbonate decomposition, water vapor driven off of the mineral feedstock by heating, and the combustion products of the fuel consumed within the cement kiln 315. The gases captured by the exhaust gas system 320 are provided to an inlet port 325 of the bioreactor 305. In some instances the gases from the exhaust gas system 320 are mixed with other gases (see FIG. 4) or further processed (see FIG. 5) before entering the bioreactor 305.

Optionally, waste gases from other sources within the facility 310 can also be captured by the exhaust gas system 320 and combined with the exhaust gas produced by the cement kiln 315, or provided separately to another port 330 of the bioreactor 305 as illustrated in FIG. 3, or combined with the gas stream from the exhaust gas system 320 in a separate gas mixing unit (see FIG. 4), or further processed (see FIG. 5) before being directed to the bioreactor 305. These other waste gases can include steam from steam-powered equipment, steam from cooling systems, exhaust from pre-heaters, chemical processes, exhaust from motors, moisture driven off as steam by a combustion or heating process and so forth.

Bioreactor 305 optionally comprises an inlet port 335 for introducing air, or other gases. Bioreactor 305 further optionally comprises an inlet port 340 for introducing molecular hydrogen from a source 345, such as source 150. Bioreactor 305 also comprises a gas vent 350 for releasing gas from a headspace 355 of the bioreactor 305 above the level of a liquid medium 360. The liquid medium 360 is introduced through a further inlet port 365 and withdrawn from an outlet port 370. Biomass 170 and/or chemical products 180 can be separated from the medium 360 removed from the bioreactor 305 with a separation system 375. The level of the liquid medium 360 relative to the positions of the various ports as illustrated in FIG. 3 is not meaningful and various substrates can either be introduced into the headspace 355 or into the liquid medium 360, such as by sparging.

In various embodiments, some or all of the gas vented through gas vent 350 can be recirculated through one or more of the inlet ports so as to increase its reaction time or effect its degree of reaction by allowing it to again traverse the liquid phase. Similarly, some or all of the liquid medium 360 that passes through the separation system 375 can be recirculated back into the bioreactor 305 through inlet port 365. In various embodiments, the biomass 170 is gasified by the cement manufacturing facility 310. Separation system 375 can employ well-known separation techniques such as fractional distillation or evaporation, pervaporation, and extractive fermentation.

FIG. 4 shows a schematic representation of an exemplary gas mixing unit 400, an optional component of systems of the invention such as systems 100 and 300. For example, the gas mixing unit 400 is optionally employed, in some embodiments, between the cement manufacturing facility 310 and the bioreactor 305. The gas mixing unit 400 can receive carbon-containing waste streams such those from the exhaust gas system 320 and other sources within cement manufacturing facility 310, optionally air or other gases, and optionally gas recirculated from the gas vent 350. The gas mixing unit 400 can mix the input gas streams to a desired proportion, such as about 60% to about 80% molecular hydrogen by volume, about 5% to about 20% carbon dioxide by volume, and about 0% to about 30% oxygen by volume.

FIG. 4 also illustrates a storage system 410 for providing a backup supply of carbon to the first substrate. The storage system 410 can store a carbon oxide containing gas, a liquid comprising an organic or inorganic carbon source, or a solid which comprises a carbon source. In some embodiments, the storage system 410 stores gases provided by the exhaust gas system 320. The storage system 410 can store this gas as a pressurized gas or as a liquefied product in various embodiments. Carbon from the storage system 410 can be dynamically added to the mixing unit 400 in response to a decrease, change in composition, or cessation of the input from any of the other sources. For instance, the input of backup carbon from the storage system 410 can be used to compensate for a decrease in carbon input when the flow of carbon from process sources is interrupted, such as when the cement making process ceases for plant maintenance or in response to a mechanical failure. In this way, growth and/or synthesis stages can continue uninterrupted in the bioreactor 110.

FIG. 5 shows a schematic representation of an exemplary gasifier 500 in combination with a steam reforming unit 510, further optional components of systems of the invention such as systems 100 and 300. The gasifier 500 receives an organic feedstock such as biomass; in some embodiments the biomass feedstock comprises biomass 170 harvested from the bioreactor 110. The gasifier 500 converts the organic feedstock into a gaseous effluent, in some embodiments through a pyrolytic reaction. The gaseous effluent from the gasifier 500 is transferred to the steam reformer 510, along with one or more optional other gas streams. For example, where the source of carbon 130 comprises a power plant, another gas stream can be steam produced from cooling water used to cool the flue gases. The output from the gasifier 500, along with any other introduced gases, are converted by the steam reformer 510 from a mix of gases primarily consisting of carbon monoxide and water, to a mix primarily composed of molecular hydrogen and carbon dioxide via the process of steam reforming. The resulting gas stream from the steam reformer 510 is a mixture of the first and second substrates and is directed to the bioreactor 110. It will be appreciated that a catalytic reformer can be used in place of steam reformer 510, in some embodiments. A catalytic reformed can use liquid water in addition to, or in place of, steam to produce the mixture of carbon dioxide and molecular hydrogen.

In addition to biomass from the bioreactor 110, other suitable feedstock for the gasifier 500 includes biomass by-products obtained during the extraction and processing of foodstuffs such as sugar from sugarcane, starch from maize corn or grains, and non-food biomass waste generated by the forestry industry. Other waste products including plastic waste, municipal waste, industrial waste, and chemical waste can also be gasified. The gas produced by the gasifier 500 can have additional gases added, such as air, oxygen, carbon dioxide and/or nitrogen in order to influence both the efficiency of the steam reformer 510 as well as to optimize the resulting mix of substrates for optimal growth of the microorganism or to maximize the production of the chemical product 180. Heat from the gasifier 500 can be used to generate power using a steam turbine, for example. In various embodiments, some of the gas produced by the gasifier 500 can be drawn off and burned rather than being directed to the steam reformer 510.

Figure 6:
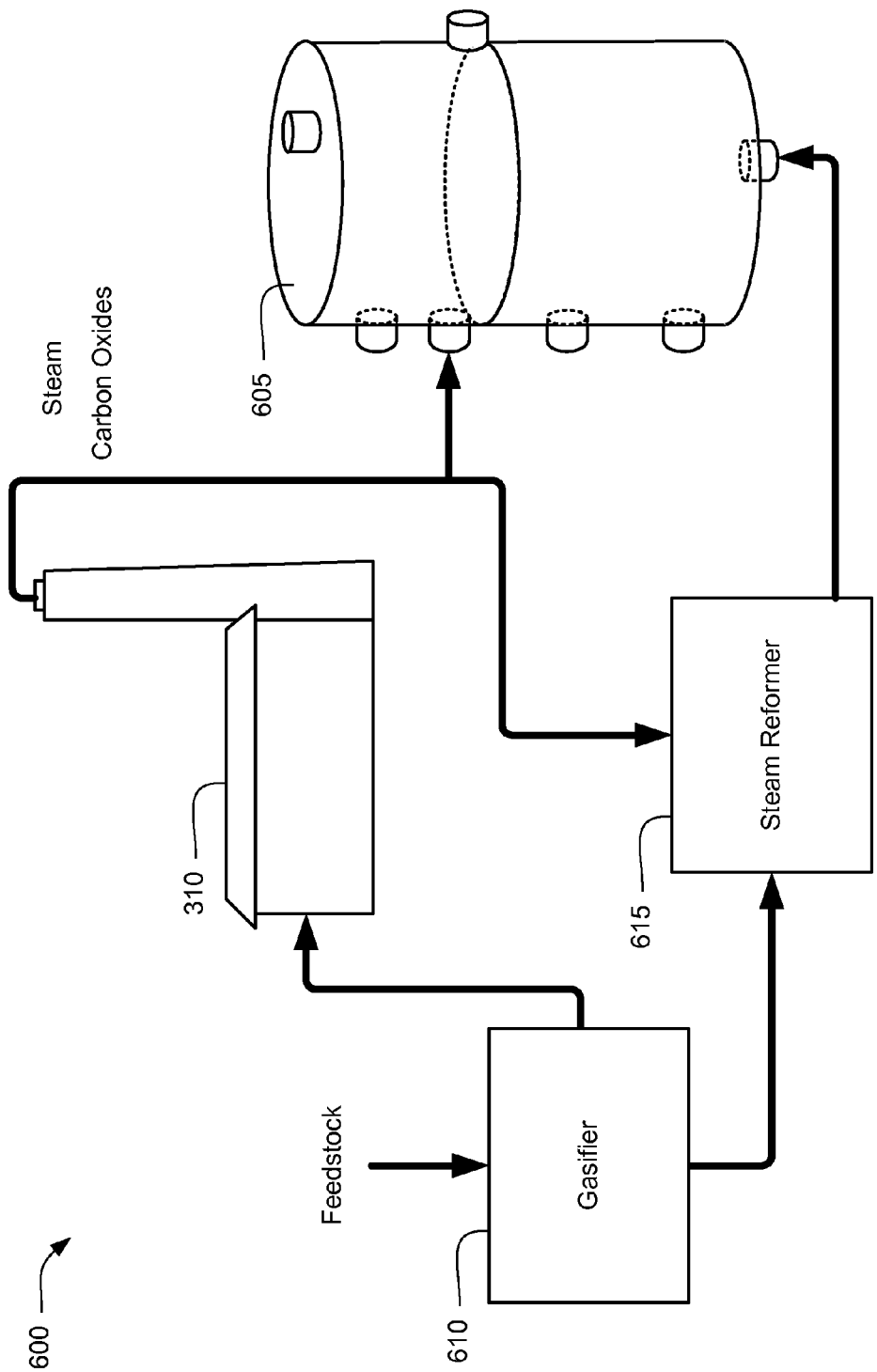
FIG. 6 is a schematic representation of a system according to another exemplary embodiment of the present invention.

FIG. 6 shows a schematic representation of another exemplary system 600 from which the production of molecular hydrogen has been omitted for clarity. The system 600 comprises a bioreactor 605 as another example of a bioreactor 110. The system 600 also comprises a cement manufacturing facility 310 which processes a mineral feedstock into cement. The bioreactor is in fluid communication with the exhaust gas system along a fluid communication path which may be direct, in that the exhaust gas goes directly into the bioreactor from the exhaust gas system, or indirect in which the path leads through one or more processing stages. The system 600 also optionally comprises a gasifier 610 that is fed an organic feedstock such as biomass 170. Heat produced by the gasifier 610 can be used in the cement manufacturing facility 310, for example, to pre-heat the mineral feedstock, or can be converted to steam or electricity to run equipment. Some of the gaseous output from the gasifier 610 can also be used by the cement manufacturing facility 310 as a fuel in the cement kiln 315, for instance.

The system 600 also optionally comprises a steam reformer 615 that receives some or all of the gaseous output from the gasifier 610, typically carbon monoxide mixed with other gases, possibly also including steam. Steam produced by the cement manufacturing facility 310, such as from process cooling water, can also be optionally fed into the steam reformer 615. Carbon oxides (predominantly carbon dioxide) from the cement manufacturing facility 310 can optionally also be fed into the steam reformer 615, fed directly into the bioreactor 605, or partially directed to each. In systems that comprise a steam reformer, and where the steam reformer receives at least some of the first gaseous stream from the cement manufacturing facility, the fluid communication path between the bioreactor and the exhaust gas system includes the steam reformer as one example of a further processing stage.

The output of the steam reformed 615 is provided as a mixture of the first and second substrates to the bioreactor 605. The bioreactor 605 can include additional ports for receiving air and/or other input gases as described above. Effluent gas from the bioreactor 605 can be recirculated as noted previously. Chemical products 180 can be added to the final cement product in order to change the color, strength, curing time, or other characteristics of the cement, in various embodiments.

In particular embodiments, the gas supplied to the steam reformer 615, or to the bioreactor 605, contains by volume at least about 5% to about 100% steam, or from about 40% to about 95% steam, or from about 40% to about 60% steam, or from about 45% to about 55% steam. In particular embodiments, the gas supplied to the steam reformer 615, or to the bioreactor 605, contains by volume about 25%, or about 30%, or about 35%, or about 40%, or about 45%, or about 50%, or about 55%, or about 60% steam.

FIG. 7 shows a schematic representation of another exemplary system 700. The system 700 is analogous to system 100 of FIG. 1 except that the source of molecular hydrogen 150 has been replaced with an electrolysis system 710 for producing molecular hydrogen by splitting water. As noted with respect to FIG. 1, the source of molecular hydrogen 150 can be a storage tank, and in these embodiments molecular hydrogen can be provided to the system 100 by truck or rail car, or by pipeline. The delivered hydrogen can be produced remotely by any number of well-known chemical processes, including electrolysis. Alternatively, the molecular hydrogen can be generated locally to the source of carbon 130 by the electrolysis system 710 which employs electricity to dissociate water molecules into molecular hydrogen and oxygen. In various embodiments, the electricity comes from a renewable source, which may or may not also be collocated with the source of carbon 130. Examples of renewable electricity sources that can be collocated, in some instances with the source of carbon 130 include solar 720 and wind 730. Other renewable electricity sources include tidal generation and geothermal generation. In those embodiments where these latter sources are not collocated with the source of carbon 130, the source of electricity can still be in electrical communication with the electrolysis system 710 over a dedicated power line or through the power grid.

Figure 8:
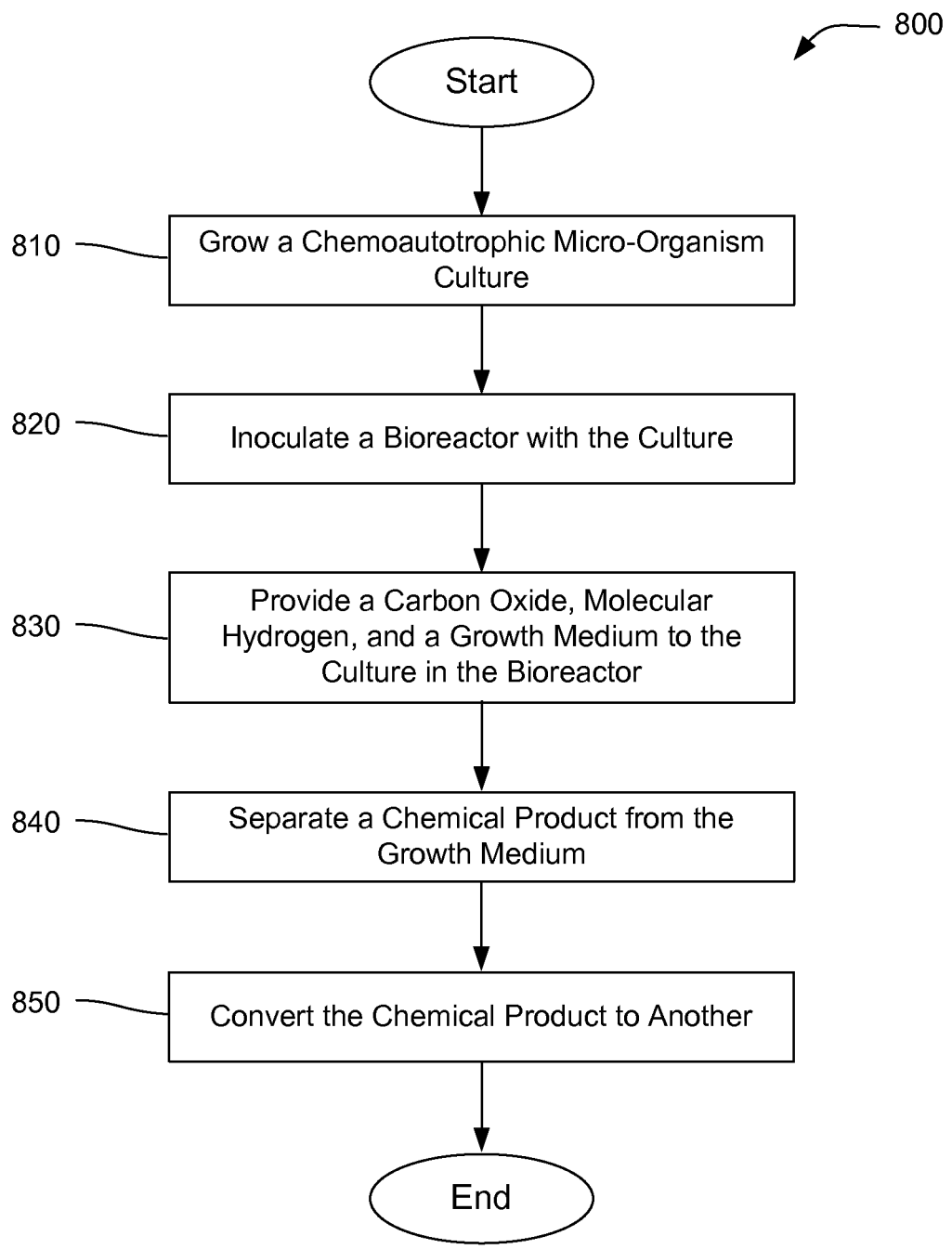
FIG. 8 is a flowchart representation of a synthesis method according to an exemplary embodiment of the present invention.

FIG. 8 illustrates an exemplary embodiment of a method 800 of the present invention. The method 800 can be used to synthesize a chemical product from carbon oxides provided by industrial waste steams or by other sources. The method 800 includes an optional step 810 of growing a chemoautotrophic micro-organism culture, an optional step 820 of inoculating a bioreactor with the chemoautotrophic micro-organism culture, a step 830 of maintaining the culture in the bioreactor by providing to the culture in the bioreactor a carbon oxide, molecular hydrogen, and a growth medium, a step 840 of separating a chemical product from the growth medium, and an optional step 850 of converting the chemical product or biomass into another substance.

Step 810 of the method 800 comprises growing a chemoautotrophic micro-organism culture. This initial step, also referred to herein as a growth stage, the chemoautotrophic micro-organism culture is grown to a suitable concentration for the subsequent steps. Step 810 can comprise providing the chemoautotrophic micro-organism culture with a solid or liquid substrate that includes one or more carbohydrates, such as fructose. Optionally, the step 810 is performed in a growth vessel, a bioreactor dedicated to growing suitable concentrations of the chemoautotrophic micro-organism. In the alternative, step 810 is performed in the same bioreactor that is used in the subsequent step 830.

Step 820 comprises inoculating a bioreactor with the chemoautotrophic micro-organism culture grown in step 810. This step can be omitted where the same bioreactor is used in steps 810 and 830. Where a growth vessel is used in step 810 and another bioreactor used in step 830, the step 820 can comprise harvesting at least some of the chemoautotrophic micro-organism culture from the growth vessel and transferring the culture to the next bioreactor.

Step 830 comprises maintaining the chemoautotrophic micro-organism culture in a bioreactor, also referred to herein as a synthesis vessel, under conditions suitable for the micro-organism to chemoautotrophically produce a chemical product. These conditions comprise a growth medium, a source of carbon, and a source of energy. Accordingly, step 830 includes providing to the culture in the bioreactor a growth medium, a carbon oxide as a source of carbon, and molecular hydrogen as a source of energy.

A suitable growth medium comprises components, such as vitamins, minerals, and micronutrients necessary and sufficient to sustain the chemoautotrophic micro-organism culture and will vary depending upon the specific chemoautotrophic micro-organism. For example, media suitable for the growth of *Rhodobacter capsulatus* are described by Madigan and Gest, "Growth of the Photosynthetic Bacteria *Rhodopsuedomonas capsulata* chemoautotrophically in the Dark with $H_2$ as the Sole Energy Source," J. of Bacteriology, 524-530 January 1979, incorporated herein by reference. Step 830, in some embodiments, does not require controlling the pH of the growth medium. Providing the growth medium in step 830 can comprise, in some embodiments, recirculating the growth medium remaining at the end of step 840, discussed below. Recirculating the growth medium can itself comprise reconditioning the growth medium by adding components (vitamins, minerals, micronutrients) thereto. An example of a vitamin that can be added is vitamin D.

Providing the carbon oxide to the bioreactor in step 830 can comprise communicating a waste stream from an industrial process to the bioreactor. Exemplary waste streams include flue gases from power plants that burn fossil fuels and gases emitted through the production of cement. Providing the carbon oxide can also comprise gasifying an organic feedstock such as a biomass, coal, fuel oil, and various waste materials comprising organic matter such as municipal waste. In various embodiments, a plurality of such sources are employed. For example, providing the carbon oxide can comprise gasifying an organic feedstock and mixing the gasified output with a waste stream from an industrial process, then communicating the resulting mixture into the bioreactor. Optionally, providing the carbon oxide can also comprise steam reforming of the industrial waste stream, the gaseous output of the gasification process, or the mixture of the two, then introducing the product of the steam reforming to the bioreactor. Optionally, in various embodiments providing the carbon oxide can comprise adding air or oxygen to any of the waste stream from the industrial process, the gasification product, the steam reforming product, or the product of mixing of any of these three, prior to introduction to the bioreactor. In various embodiments, providing the carbon oxide in step 830 further comprises cooling the waste gas, the product of the gasification, the product of the steam reforming, or a mixture of any of these. In some of these embodiments cooling is performed with water to generate steam. In some of these further embodiments the step 830 includes using the steam in the steam reforming process.

In some embodiments providing the carbon oxide comprises saturating a liquid medium with the waste stream gas, or with the gaseous product of the gasification step, or with the gaseous product of the steam reforming, or with a mixture thereof, and then introducing the saturated liquid medium into the bioreactor. In other embodiments, providing the carbon oxide comprises introducing the waste stream gas, or the gaseous product of the gasification step, or the gaseous product of the steam reforming, or a mixture thereof, as a gas into the bioreactor by sparging or micro-bubble dispersion, for example.

In those embodiments in which the carbon oxide is introduced to the bioreactor in step 830 as a gas, the carbon oxide-containing gas can comprise carbon monoxide at a concentration of at least about 20% to about 100% by volume. In other embodiments, the carbon monoxide is provided at a concentration of from about 40% to about 95% carbon monoxide by volume, or at a concentration of from about 40% to about 60% carbon monoxide by volume, or at a concentration of from about 45% to about 55% carbon monoxide by volume. In still other embodiments the carbon monoxide concentration is about 25%, about 30%, about 35%, about 40%, about 45%, about 50%, about 55%, or about 60% by volume. In yet other embodiments the carbon oxide-containing gas provided to the bioreactor in step 830 comprises about 6% carbon monoxide by volume, and either the same gas or another gas provided to the bioreactor comprises molecular hydrogen and/or hydrogen sulfide and/or carbon dioxide.

In those embodiments in which the carbon oxide is introduced to the bioreactor in step 830 as a gas, the carbon oxide-containing gas can comprise carbon dioxide at a concentration of at least about 5% to about 100% by volume. In other embodiments, the carbon dioxide is provided at a concentration of from about 40% to about 95% carbon dioxide by volume, or at a concentration of from about 40% to about 60% carbon dioxide by volume, or at a concentration of from about 45% to about 55% carbon dioxide by volume. In still other embodiments the carbon dioxide concentration is about 25%, or about 30%, or about 35%, or about 40%, or about 45%, or about 50%, or about 55%, or about 60% by volume. In some of these embodiments the carbon dioxide concentration is either partially or entirely derived from cement production.

Step 830 also comprises introducing molecular hydrogen to the bioreactor. In some embodiments, introducing molecular hydrogen to the bioreactor includes receiving the molecular hydrogen as a compressed gas or liquid, by truck, rail car, or pipeline for example, storing the molecular hydrogen in a storage tank, and communicating the molecular hydrogen from the storage tank to the bioreactor. In other embodiments, introducing molecular hydrogen to the bioreactor includes generating the molecular hydrogen. Various chemical and electro-chemical processes produce hydrogen, including steam reforming and the electrolysis of water. In some instances the electrolysis is performed in an electrolysis system disposed external to the bioreactor while in other instances the electrolysis is performed within the bioreactor as described, for example, in U.S. patent application Ser. No. 13/204,649, noted previously. In either case, electricity to split the water can be purchased from an electric utility or generated locally, or both. Where the electricity generation is collocated with the bioreactor generating the molecular hydrogen includes generating electricity and using the electricity to electrolyze water to generate molecular hydrogen and molecular oxygen. At least some of the generated molecular oxygen, in various embodiments, is communicated to the bioreactor, vented to the atmosphere, used in an industrial process such as to burn fuel in a cement kiln, compressed and sold, or any combination thereof.

In those embodiments in which the molecular hydrogen is introduced to the bioreactor in step 830 as a gas, the molecular hydrogen-containing gas can comprise molecular hydrogen at a concentration of at least about 20% to about 100% by volume. In other embodiments, the molecular hydrogen is provided at a concentration of from at least about 5% to about 95% molecular hydrogen by volume, or at a concentration of from about 40% to about 95% molecular hydrogen by volume, or at a concentration of from about 20% to about 80% molecular hydrogen by volume, or at a concentration of from about 40% to about 60% molecular hydrogen by volume, or at a concentration of from about 45% to about 55% molecular hydrogen by volume. In still other embodiments the molecular hydrogen concentration is about 25%, or about 30%, or about 35%, or about 40%, or about 45%, or about 50%, or about 55%, or about 60% by volume. In further embodiments the molecular hydrogen is provided at a concentration of about 6% by volume, and carbon monoxide and/or hydrogen sulfide and/or methane are also added to the bioreactor.

In addition to providing carbon monoxide and/or carbon dioxide and molecular hydrogen, in various embodiments step 830 also comprises adding another gas to the bioreactor, where the other gas can include all or any combination of air, methane, hydrogen sulfide, and molecular oxygen. Exemplary concentrations of molecular oxygen are about 0% to about 1% by volume, from about 1% to about 10% by volume, from about 10% to about 16% by volume, and from about 16% to about 30% by volume. In some embodiments, the concentration of molecular oxygen is about 0%, or about 1%, or about 5%, or about 8%, or about 10%, or about 16% by volume.

Either or both of steps 810 and 830 optionally can include exposing the culture to light. Exposure to light can aid in the microbial synthesis of various vitamins, such as vitamin D, which can promote better growth. Light exposure can also stimulate or influence a metabolic pathway of the microorganisms to select for, or encourage the production of, specific compounds or compound types as the chemical product 180.

Step 840 comprises separating a chemical product from the growth medium. In various embodiments the bioreactor is configured to perform the separation, while in other embodiments the step includes withdrawing growth medium from the bioreactor and passing the growth medium through a separation system. Exemplary separation systems employ well-known techniques such as fractional distillation or evaporation, pervaporation, and extractive fermentation. In some embodiments a biomass is additionally separated from the growth medium in step 840. Exemplary chemical products that can be produced by the method 800 include hydroxyalkanoates and polyhydroxyalkanoates such as propanediol, octadecane 1,12 diol, carotenoids, fatty acids, fats, oils, and alkanes. Chemical products 180 can also comprise, in some embodiments, carotenoids, lipopolysaccharides, a mixed alcohol stream containing one or more alkanoate diols and one or more other alcohols, or a variety of other chemicals, and can be recovered from the chemoautotrophic synthesis broth by methods known in the art. By-products such as acids including acetate and butyrate may also be recovered from the culture broth using methods known in the art. Biomass 170 harvested from the bioreactor 110 can also be a useful commodity as it can be converted to biofuel, used as animal feed, as a colorant, as an additive for products for use with humans and/or animals for cosmetic or nutritional purposes, turned to compost, gasified, and so forth.

As noted above, the growth medium obtained from the separation step 840 can be recirculated, in some embodiments, back into the bioreactor, and biomass obtained from the step 840 is optionally gasified in step 830. In an optional step 850 the chemical product or biomass obtained in step 840 can be converted into another product. Examples of products that can be synthesized in step 850 include biofuels and polytrimethylene terephthalate.

Figure 9:
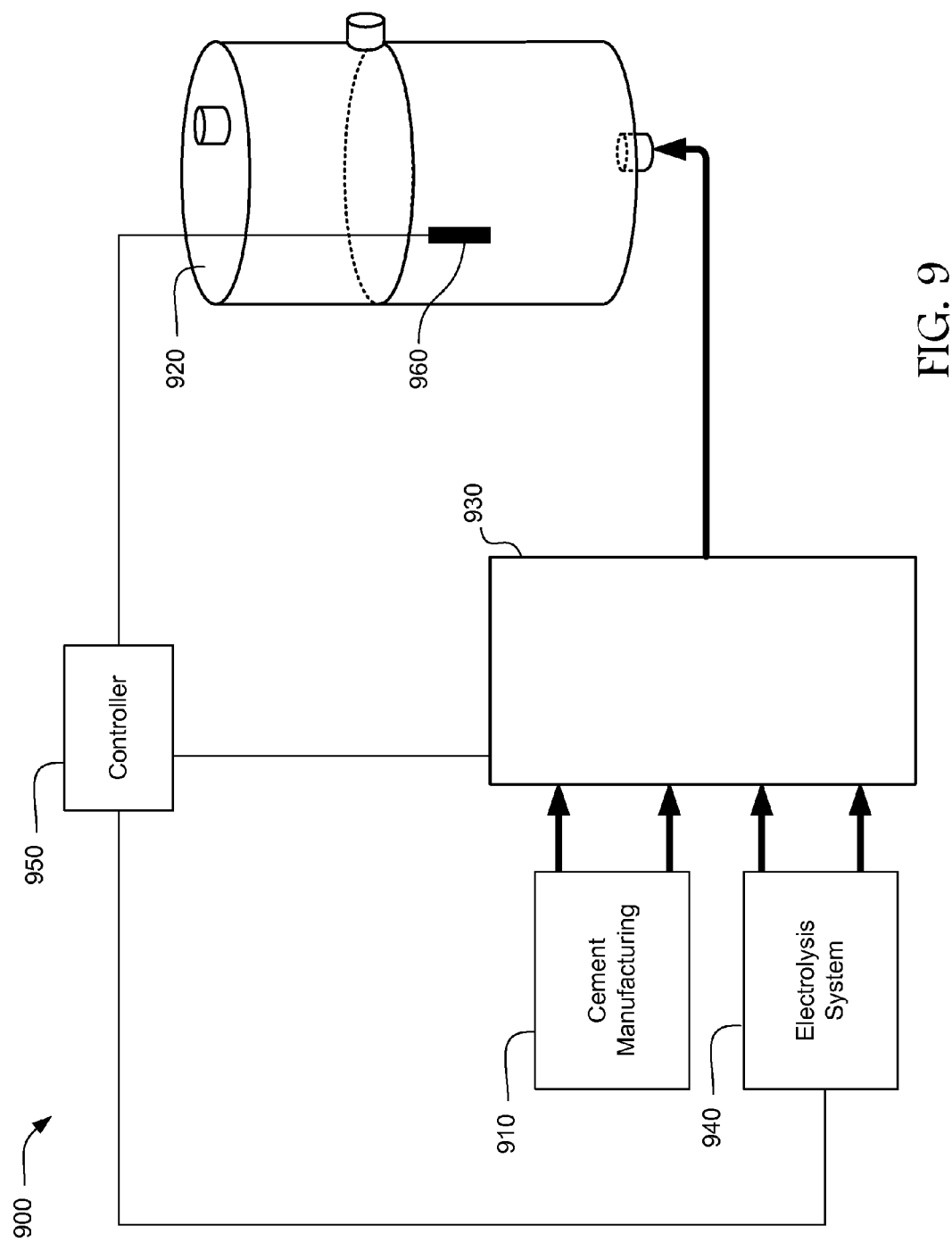
FIG. 9 is a schematic representation of a system according to another exemplary embodiment of the present invention.

FIG. 9 shows a schematic representation of another exemplary system 900 of the present invention. The system 900 comprises a cement manufacturing facility 910 and a bioreactor 920, both as described elsewhere herein. The system 900 also comprises a gas mixing unit 930 in fluid communication with the cement manufacturing facility 910 in order to receive exhaust gases from the cement kiln and optionally other gas streams from the cement manufacturing facility 910 including steam and exhaust gases from other sources such as pre-heaters and motor-driven equipment. Gas streams from the cement manufacturing facility 910 can also be reformed prior to entering the gas mixing unit 930. The gas mixing unit 930 is also in fluid communication with the bioreactor 920 so that the output from the gas mixing unit 930 is directed into the bioreactor 920.

The system also comprises an electrolysis system 940 that produces streams of both molecular hydrogen and oxygen; the electrolysis system 940 is also in fluid communication with the gas mixing unit 930. The electricity used to dissociate water in the electrolysis system 940 can be supplied from the electric utility grid, or from a dedicated source of renewable power, as discussed above. The molecular hydrogen produced by the electrolysis system 940 is directed to the gas mixing unit 930, and in some embodiments the molecular oxygen produced by the electrolysis system 940 is also directed to the gas mixing unit 930. Any of the various gas streams from the cement manufacturing facility 910 may be mixed prior to their receipt by the gas mixing unit 930, and likewise, any of the gas streams from the cement manufacturing facility 910 may be independently received by the gas mixing unit 930. Similarly, the molecular hydrogen and oxygen from the electrolysis system 940 can be mixed or received independently at the gas mixing unit 930.

The system 900 also optionally includes a controller 950 configured to regulate the flow of gases into the gas mixing unit 930 by independently controlling the inputs from the cement manufacturing facility 910 and the electrolysis system 940. The gas mixing unit 930 is not limited to receiving gases from the cement manufacturing facility 910 and the electrolysis system 940 and may also include the ability to receive and regulate gases from third sources including the atmosphere. Exhaust gas from the bioreactor 920 can also be recirculated back through the bioreactor 920 by addition back into the gas mixing unit 930.

In some embodiments, the controller 950 monitors the conditions within the bioreactor 920 through the use of one or more sensors 960 optionally disposed within the bioreactor 920, either in the aqueous medium, the headspace above, or both. In some instances, where the controller 950 is not admitting to the gas mixing unit 930 as much of a gas stream as is being produced, the excess gas from the stream may be vented to the atmosphere, as in the case with excess molecular oxygen from electrolysis system 940 or stored in a storage system 410 (FIG. 4) where the excess gas includes a carbon oxide. Conditions that can be monitored by sensors 960 and used to regulate the incoming gases to the gas mixing unit 930 include temperature, acidity, pressure, and the concentrations of one or more gases in the headspace, in the incoming mix, or dissolved in the aqueous medium. In some embodiments, the controller 950 optionally is configured to regulate the electrolysis system 940 to generate only as much molecular hydrogen as is required at the gas mixing unit 930. In various embodiments the controller 950 is configured to maintain an output from the gas mixing unit that comprises about 60 to about 80% molecular hydrogen by volume, about 5% to about 20% carbon dioxide by volume, and about 0% to about 30% molecular oxygen by volume.

The controller 950 can comprise hardware such as an ASIC or an FPGA, firmware, and/or a microprocessor configured to execute software stored on a computer readable medium, or combinations thereof. A computer readable medium can comprise a non-transitory memory device. The controller 950 can therefore comprise a computing device such as a PC, tablet, or server running control software.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A system comprising:
   a cement manufacturing facility including a cement kiln and an exhaust gas system configured to capture the exhaust gas from the cement kiln;
   a bioreactor system including a bioreactor in fluid communication with the exhaust gas system and configured to produce a chemical product from a carbon oxide in a first gaseous stream from the exhaust gas system, the first gaseous stream including the exhaust gas from the cement kiln;
   a gas mixing unit in fluid communication between the exhaust gas system and the bioreactor; and
   an electrolysis system configured to produce a molecular hydrogen stream, wherein the gas mixing unit is configured to receive the molecular hydrogen stream, wherein the electrolysis system is configured to produce a molecular oxygen stream, and wherein the gas mixing unit is configured to receive the molecular oxygen stream independent from the molecular hydrogen stream.

2. The system of claim 1 further comprising
   a gasifier configured to generate a second gaseous stream, and
   a reformer configured to receive the second gaseous stream and to produce a third gaseous stream, wherein the bioreactor is in fluid communication with the reformer to receive the third gaseous stream.

3. The system of claim 2 wherein the reformer is further configured to receive at least some of the first gaseous stream from the cement manufacturing facility such that a fluid communication path between the bioreactor and the exhaust gas system includes the reformer.

4. The system of claim 2 wherein the reformer comprises a steam reformer.

5. The system of claim 1 wherein the bioreactor system includes a separation system configured to receive a liquid medium directly from the bioreactor and to separate the chemical product from the received liquid medium.

6. The system of claim 1 further comprising a controller configured to monitor a condition in the bioreactor and further configured to regulate the flow of gases into the gas mixing unit responsive to the condition.

7. The system of claim 1 further comprising a storage system in fluid communication with the gas mixing unit, the storage system being configured to provide a backup supply of the carbon oxide to the gas mixing unit.

8. The system of claim 1 wherein the electrolysis system is disposed within the bioreactor.

9. The system of claim 1 wherein the cement manufacturing facility further includes a motor and the exhaust gas system is further configured to capture the exhaust gas from the motor.

10. The system of claim 1 further comprising a controller configured to regulate the flow of the molecular hydrogen stream and the flow of the exhaust gas into the gas mixing unit.

11. The system of claim 10 wherein the gas mixing unit is further configured to receive air through an input that is separate from inputs for the molecular hydrogen stream and for the flow of exhaust gas, and wherein the controller is further configured to regulate the flow of air into the gas mixing unit while admitting the molecular hydrogen stream into the gas mixing unit.

12. The system of claim 1 wherein the cement manufacturing facility further includes a motor and the gas mixing unit is further configured to receive exhaust gas from the motor independently from the exhaust gas from the cement kiln and configured to mix the exhaust gas from the motor with the exhaust gas from the cement kiln to a desired proportion.

13. The system of claim 12 wherein the gas mixing unit is further configured to receive molecular hydrogen independently from the exhaust gas from the cement kiln and the exhaust gas from the motor and configured to mix the molecular hydrogen with the exhaust gas from the motor and with the exhaust gas from the cement kiln to a desired proportion.

14. A system comprising:
a cement manufacturing facility including a cement kiln and an exhaust gas system configured to capture the exhaust gas from the cement kiln;
a bioreactor system including a bioreactor in fluid communication with the exhaust gas system and configured to produce a chemical product from a carbon oxide in a first gaseous stream from the exhaust gas system, the first gaseous stream including the exhaust gas from the cement kiln;
a gas mixing unit in fluid communication between the exhaust gas system and the bioreactor, the gas mixing unit being further configured to receive air through an input that is separate from inputs for the molecular hydrogen stream and for the flow of exhaust gas;
an electrolysis system configured to produce a molecular hydrogen stream, and wherein the gas mixing unit is configured to receive the molecular hydrogen stream; and
a controller configured to regulate the flow of the molecular hydrogen stream and the flow of the exhaust gas into the gas mixing unit, wherein the controller is further configured to regulate the flow of air into the gas mixing unit while admitting the molecular hydrogen stream into the gas mixing unit.

15. The system of claim 14 further comprising
a gasifier configured to generate a second gaseous stream, and
a reformer configured to receive the second gaseous stream and to produce a third gaseous stream, wherein the bioreactor is in fluid communication with the reformer to receive the third gaseous stream.

16. The system of claim 15 wherein the reformer is further configured to receive at least some of the first gaseous stream from the cement manufacturing facility such that a fluid communication path between the bioreactor and the exhaust gas system includes the reformer.

17. The system of claim 15 wherein the reformer comprises a steam reformer.

18. The system of claim 14 wherein the bioreactor system includes a separation system configured to receive a liquid medium directly from the bioreactor and to separate the chemical product from the received liquid medium.

19. The system of claim 14 wherein the controller is further configured to monitor a condition in the bioreactor and further configured to regulate the flow of gases into the gas mixing unit responsive to the condition.

20. The system of claim 14 further comprising a storage system in fluid communication with the gas mixing unit, the storage system being configured to provide a backup supply of the carbon oxide to the gas mixing unit.

21. The system of claim 14 wherein the electrolysis system is disposed within the bioreactor.

22. The system of claim 14 wherein the cement manufacturing facility further includes a motor and the exhaust gas system is further configured to capture the exhaust gas from the motor.

23. The system of claim 14 wherein the cement manufacturing facility further includes a motor and the gas mixing unit is further configured to receive exhaust gas from the motor independently from the exhaust gas from the cement kiln and configured to mix the exhaust gas from the motor with the exhaust gas from the cement kiln to a desired proportion.

24. The system of claim 23 wherein the gas mixing unit is further configured to receive molecular hydrogen independently from the exhaust gas from the cement kiln and the exhaust gas from the motor and configured to mix the molecular hydrogen with the exhaust gas from the motor and with the exhaust gas from the cement kiln to a desired proportion.

* * * * *